(12) United States Patent
Dreyfuss et al.

(10) Patent No.: US 7,691,847 B2
(45) Date of Patent: Apr. 6, 2010

(54) METHOD OF TREATING NEUROLOGICAL DISEASES AND DISORDERS

(75) Inventors: Gideon Dreyfuss, Wynnewood, PA (US); Jin Wang, Lawrenceville, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 799 days.

(21) Appl. No.: 10/532,203

(22) PCT Filed: Oct. 17, 2003

(86) PCT No.: PCT/US03/33022

§ 371 (c)(1),
(2), (4) Date: Jan. 9, 2006

(87) PCT Pub. No.: WO2004/036181

PCT Pub. Date: Apr. 29, 2004

(65) Prior Publication Data

US 2006/0135509 A1    Jun. 22, 2006

(51) Int. Cl.
*A01N 43/46* (2006.01)
*A61K 31/54* (2006.01)
*C07D 279/00* (2006.01)
*C07D 279/18* (2006.01)
*C07D 279/22* (2006.01)

(52) U.S. Cl. ............ 514/217; 514/224.8; 544/14; 544/35; 544/39

(58) Field of Classification Search ........ 514/217, 514/224.8; 544/14, 35, 38
See application file for complete search history.

(56) References Cited

U.S. PATENT DOCUMENTS 5,576,328 A   11/1996   Herbert et al. ........... 514/301
6,117,866 A    9/2000   Bondinell et al. ........ 514/221

OTHER PUBLICATIONS

Chang et al. PNAS 2001, vol. 98, No. 17, pp. 9808-9813.*

* cited by examiner

*Primary Examiner*—Sreeni Padmanabhan
*Assistant Examiner*—Samira Jean-Louis

(57) ABSTRACT

The present invention provides methods for treating neurological diseases and disorders. Compounds that replace or enhance the function of SMN or alleviate or reduce a phenotype of cells with low SMN protein levels are provided. Screening methods and kits for identifying such compounds also are provided.

1 Claim, No Drawings

METHOD OF TREATING NEUROLOGICAL DISEASES AND DISORDERS

BACKGROUND OF THE INVENTION

Loss of neurons by a degenerative process is a pathological feature of many human neurological disorders. Neuronal cell death is a normal part of tissue development and maintenance. Abnormal neuronal cell death, however, occurs as a result of a variety of conditions including, but not limited to, traumatic injury or trauma, ischemia, and neurodegenerative diseases such as Parkinson's disease, Huntington's disease, Alzheimer's disease, amyotrophic lateral sclerosis (ALS), and stroke.

Spinal muscular atrophy (SMA) (Roberts, et al. (1970) *Arch. Dis. Child.* 45:33-38), an autosomal recessive disease with characteristics of motor neuron degeneration and muscle atrophy, is a common childhood genetic disorder and the most frequent genetic cause of infant mortality (Roberts, et al. (1970) ibid.; Pearn, J. (1980) *Lancet* 1:919-922; Czeizel and Hamula (1989) *J. Med. Genet.* 26:761-763). Based on the age of onset and the severity of the disease, SMA is classified as severe type I (Werdnig-Hoffman disease), moderate type II, or mild type III (Kugelberg-Welander disease). The survival motor neuron (SMN) gene has been linked to SMA. The human genome contains two copies of the SMN gene because of an inverted duplication at 5q13. This phenomenon appears to be human-specific as all other organisms examined to date have a single copy of SMN. Deletions or mutations of the telomeric SMN1 gene, which result in reduced SMN protein level, have been found in the vast majority of SMA patients (Cobben, et al. (1995) *Am. J. Hum. Genet.* 57:805-808; Bussaglia, et al. (1995) *Nat. Genet.* 11:335-337; Hahnen, et al. (1995) *Hum. Mol. Genet.* 4:1927-1933; Rodrigues, et al. (1995) *Hum. Mol. Genet.* 4:631-634; Lefebvre, et al. (1995) *Cell* 80:155-165; Chang, et al. (1995) *Am. J. Hum. Genet.* 57:1503-1505; Hahnen, et al. (1996) *Am. J. Hum. Genet.* 59:1057-1065; Velasco, et al. (1996) *Hum. Mol. Genet.* 5:257-263).

One strategy for the treatment of SMA has been to increase the amount of SMN protein. As SMA patients have a functional centromeric copy of the gene, referred to as smn2, investigations have been conducted to identify compounds that shift the alternative splicing pattern of the SMN2-derived pre-mRNA, which normally primarily produces exon7-deleted non-functional SMN protein, to increase the production of full-length SMN (Chang, et al. (2001) *Proc. Natl. Acad. Sci. U.S.A.* 98:9808-9813; Andreassi, et al. (2001) *Hum. Mol. Genet.* 10:2841-2849). To date, the compounds identified in these screens, aclarubicin and butyric acid, are either very toxic or too pleiotropic and carry a very high risk of serious side effects.

Although motor neurons are the only known cell type to be effected in SMA patients, SMN protein is expressed ubiquitously in all tissues and cell types examined (Lefebvre, et al. (1995) *Cell* 80:155-165; Lefebvre, et al. (1997) *Nat. Genet.* 16:265-269; Coovert, et al. (1997) *Hum. Mol. Genet.* 6:1205-1214). SMN is believed to participate in several divergent cellular processes. For example, in addition to its cytoplasmic localization, SMN is also found in a subnuclear structure, referred to as gems, which is found in the vicinity of, and often overlaps with, coiled bodies (Liu, et al. (1997) *Cell* 90:1013-1021). The function of coiled bodies is unknown. However, they are known to contain spliceosomal small nuclear ribonucleoprotein particles (snRNPs), which function in pre-mRNA splicing, and components of small nucleolar ribonucleoprotein particles, which are involved in pre-rRNA processing. Therefore, coiled bodies have been suggested to play a role or roles in snRNP and small nucleolar ribonucleoprotein particle metabolism (Gall, et al. (1995) *Dev. Genet.* 16:25-35). Because gems and coiled bodies are often associated and contain similar sets of proteins and RNAs, it is believed that they have related functions. Moreover, SMN has been shown to interact with a group of Sm proteins, the core proteins of snRNPs, and a protein, Gemin2, formerly known as SIP1, both in vitro and in vivo (Liu, et al. (1997) supra). Injection of antibodies against either SMN or Gemin2 into *Xenopus* oocytes inhibits assembly and import of snRNPs, thus indicating that the SMN-Gemin2 complex performs an important function in snRNP metabolism (Fischer, et al. (1997) *Cell* 90:1023-1029; Buhler, et al. (1999) *Hum. Mol. Genet.* 8:2351-2357). A dominant negative mutant of SMN, SMNN27, also inhibits snRNP assembly in the cytoplasm (Pellizzoni, et al. (1998) *Cell* 95:615-624). Moreover, the nuclear pool of SMN protein was found to be required for pre-mRNA splicing, which may facilitate regeneration or recycling of snRNPs in the nucleus (Pellizzoni, et al. (1998) ibid.). Recently, two additional proteins, Gemin3 and Gemin4, which are associated with SMN, were described (Charroux, et al. (1999) *J. Cell Biol.* 147:1181-1194; Charroux, et al. (2000) *J. Cell Biol.* 148:1177-1186). SMN may also be involved in regulation of gene expression by interacting with transcriptional activators (Strasswimmer, et al. (1999) *Hum. Mol. Genet.* 8:1219-1226; Campbell, et al. (2000) *Hum. Mol. Genet.* 9:1093-1100; Williams, et al. (2000) *FEBS Lett.* 470:207-210). The ability of SMN to directly bind RNA, along with its close localization to microtubules in the cytoplasm and neuronal dendrites and axons, indicates that SMN may be involved in the transport of RNA (Lorson and Androphy (1998) *Hum. Mol. Genet.* 7:1269-1275; Bechade, et al. (1999) *Eur. J. Neurosci.* 11:293-304; Bertrandy, et al. (1999) *Hum. Mol. Genet.* 8:775-782; Pagliardini, et al. (2000) *Hum. Mol. Genet.* 9:47-56). As a means of better defining the function of SMN and for screening for compounds which can substitute for SMN function, Wang and Dreyfuss ((2001) *J. Biol. Chem.* 276:9599-9605) developed a cell line which is deficient in endogenous SMN and expresses exogenous SMN under the control of a tetracycline-repressible promoter.

Psychiatric disorders are pathological conditions of the brain characterized by identifiable symptoms that result in abnormalities in cognition, emotion or mood, or the highest integrative aspects of behavior. These disorders may vary in severity of symptoms, duration, and functional impairment. Psychiatric disorders afflict millions of people worldwide resulting in tremendous human suffering and economic burden due to lost productivity.

Inappropriate treatment of these diseases seriously compromises the patient's quality of life, causing emotional suffering and increasing the risk of lost livelihood and disrupting social integration. In the most severe cases these disorders can lead to suicide.

Over the past several decades, the use of pharmacological agents to treat psychiatric disorders has greatly increased. The reason for this increase is largely due to research advances in both neuroscience and molecular biology. In addition, compounds have been generated that are more effective therapeutic agents with fewer side effects, targeted to correct the biochemical alterations that accompany mental disorders.

Calmidazolium and W7, potent inhibitors of calmodulin (CaM), protect pyramidal cells in the CA1 region of the hippocampus against hypoxia/hypoglycemia (Sun, et al. (1997) *Neuroreport* 8:415-418). Furthermore, calmidazolium and KN-93, a $Ca^{2+}$/CaM-dependent protein kinase II (CaMKII)-specific inhibitor, block long-term depression (Margrie, et al. (1998) *Nat. Neurosci.* 1:378-383). A number of clinically-effective antipsychotic drugs also bind to calmodulin (Weiss, et al. (1980) *Adv. Cyclic Nucleotide Res.* 12:213-225).

Despite advances that have occurred from a better understanding of neuropharmacology, however, many neurological and psychiatric diseases remain untreated or inadequately treated with current pharmaceutical agents. Accordingly, there is a need for antineurodegenerative and psychopharmacological agents that are effective in the treatment of neurological and psychiatric disorders.

It has now been found that various compounds typically categorized as an antidepressant, antipsychotic, antihistamine, anticholinergic, antiparkinsonian, neuroleptic, adrenergic blocker, muscle relaxant, vasodilator, antihyperlipoproteinemic, antispasmodic, platelet aggregation inhibitor, oxytocin, antitussive, antipruritic, antiemetic, sedative, hypnotic, respiratory stimulant, or antiserotonin exhibit the ability to replace or enhance the function of SMN. These compounds are thus useful broadly in the treatment of neurodegenerative diseases and disorders. The invention also the invention provides methods and kits for identifying additional compounds and using such compounds in the treatment of neurological and psychiatric diseases and disorders.

SUMMARY OF THE INVENTION

The present invention provides methods of treating a patient having a neurological or psychiatric disease or disorder. The methods comprise administering an effective amount of a compound that replaces or enhances the function of SMN to alleviate or reduce a phenotype of a cell with low SMN protein levels.

Methods and kits for identifying such compounds as well as exemplary compounds identified as having these activities are provided.

DETAILED DESCRIPTION OF THE INVENTION

The present invention relates to methods of treating neurological diseases and disorders and psychiatric diseases and disorders as well as kits for identifying therapeutic agents useful in these methods.

Neurological diseases and disorders, as used herein, is used in the broadest sense and includes neurodegenerative diseases and disorders. As defined herein, a neurodegenerative disease or disorder may be characterized by the manifestation of gross physical dysfunction, not otherwise determinable as having emotional or psychiatric origins, typically resulting from progressive and irreversible loss of neurons. Such neurodegenerative diseases and disorders are defined in The Diagnostic and Statistical Manual of Mental Disorders-IV (DSM-IV) (American Psychiatric Association (1995)) and include, but are not limited to, Primary Lateral Sclerosis (PLS), Progressive Muscular Atrophy (PMA), Amyotrophic Lateral Sclerosis (ALS), Alzheimer's disease, Pick's disease, Huntington's disease, and Parkinson's disease. Of particular interest in the present invention are those diseases or disorders resulting from an alteration of normal SMN-associated processes including, but not limited to, SMA1 (Spinal Muscular Atrophy I, Werdnig-Hoffmann Disease, Infantile Muscular Atrophy), SMA2 (Spinal Muscular Atrophy II, Spinal Muscular Atrophy, Mild Child and Adolescent Form), SMA3 (Spinal Muscular Atrophy III, Juvenile Spinal Muscular Atrophy, Kugelberg-Welander Disease), and SMA4 (Spinal Muscular Atrophy IV).

A psychiatric disease or disorder, as used herein, may be characterized as one which is of emotional or psychiatric origin and is typically not associated with a loss of neurons. Exemplary psychiatric diseases and disorders include, but are not limited to, eating disorders, such as anorexia nervosa, bulimia nervosa, and atypical eating disorder; mood disorders, such as recurrent depressive disorder, bipolar affective disorder, persistent affective disorder, and secondary mood disorder; drug dependency such as alcoholism; neuroses, including anxiety, obsessional disorder, somatoform disorder, and dissociative disorder; grief; post-partum depression; psychosis such as hallucinations and delusions; dementia; paranoia; Tourette's syndrome; attention deficit disorder; psychosexual disorders, schizophrenia; and sleeping disorders.

One embodiment of the invention provides a method of treating a patient having a neurodegenerative disease or disorder, comprising administering a compound that replaces or enhances the function of SMN to alleviate or reduce a cellular phenotype associated with low levels of SMN protein. By "replaces or enhances the function of SMN" it is meant that a compound may be able to physically substitute for SMN in an SMN-associated complex; may activate another protein to functionally replace SMN in an SMN-associated processes; may functionally bypass SMN; may enhance the amount of SMN protein by, for example, decreasing SMN protein turnover; or may stimulate or modulate the activity of existing SMN protein to overcome low SMN protein levels. In a preferred embodiment, a compound which replaces or enhances the function of SMN does so without significantly altering SMN protein levels. Cellular phenotypes typically associated with low levels of SMN protein include, but are not limited to, poor cell viability and/or proliferation and high cell death. Accordingly, compounds which alleviate or reduce a cellular phenotype associated with low levels of SMN protein should increase viability and/or proliferation and decrease cell death. Exemplary compounds with such activity are provided.

Compounds, as described herein, include all enantiomers, isomers or tautomers, as well as any derivatives of such compounds that retain the same biological activity as the original compound.

In one embodiment a compound that may be used in accordance with the methods of the invention comprises a structure of Formula I:

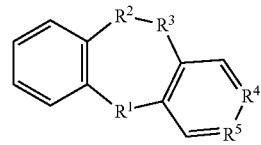

FORMULA I

Exemplary compounds comprising the structure of Formula I which depict various substituent R groups include, but are not limited to, the following:

Compound 1
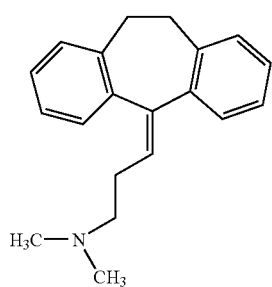
Compound 2
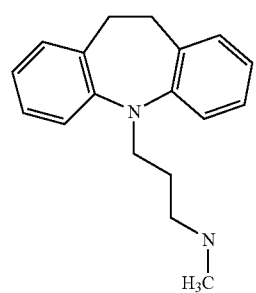
Compound 3
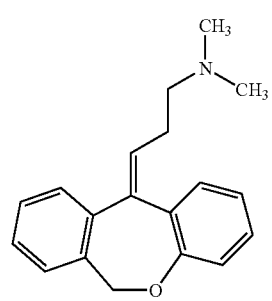
Compound 4
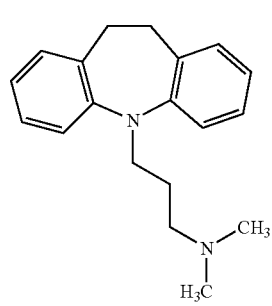
Compound 5
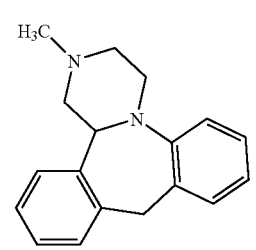
-continued
Compound 6
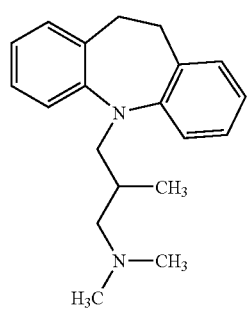
Compound 7
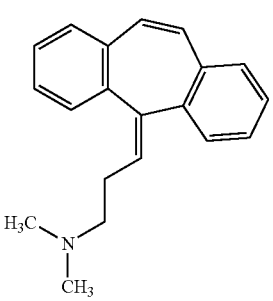
Compound 8
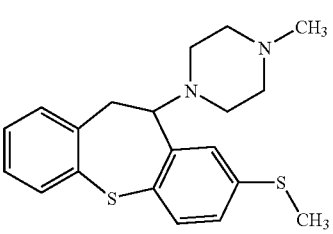
Compound 9
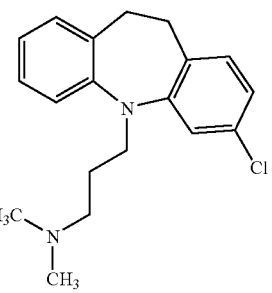
Compound 10
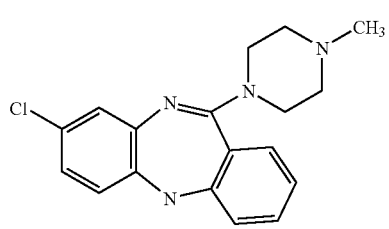
and pharmaceutically acceptable salts and complexes thereof.
In another embodiment, a compound that may be used in accordance with the methods of the invention comprises a structure of Formula II:

FORMULA II

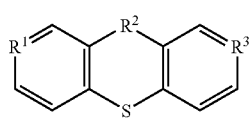

Exemplary compounds comprising the structure of Formula II which depict various substituent R groups include, but are not limited to, the following:

Compound 11

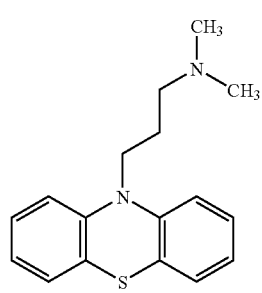

Compound 12

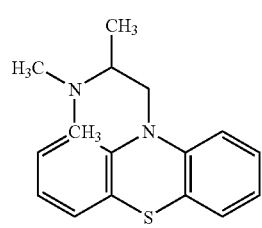

Compound 13

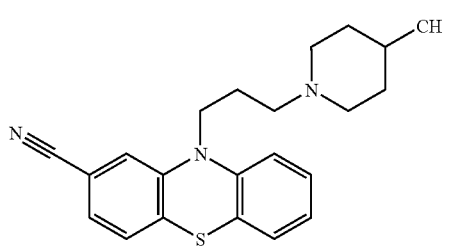

Compound 14

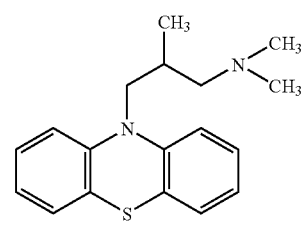

Compound 15

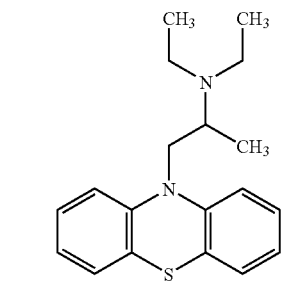

Compound 16

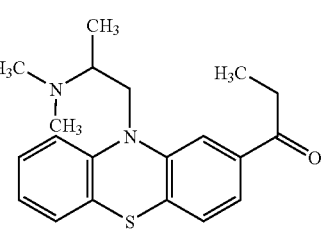

Compound 17

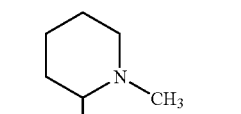

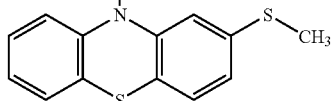

Compound 18

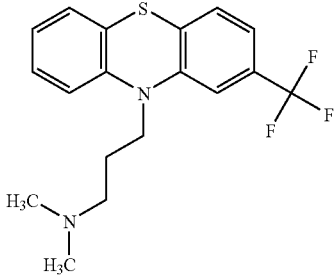

Compound 19

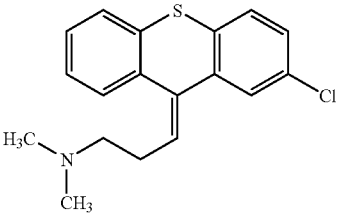

Compound 20 and pharmaceutically acceptable salts and complexes thereof.

In yet another embodiment, a compound that may be used in accordance with the methods of the invention comprises a structure of Formula III:

FORMULA III

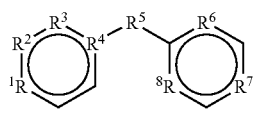

Exemplary compounds comprising the structure of Formula III which depict various substituent R groups include, but are not limited to, the following:

Compound 21

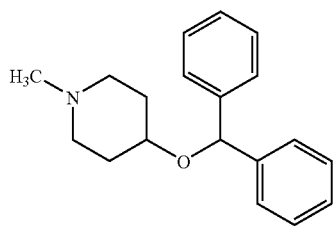

Compound 22

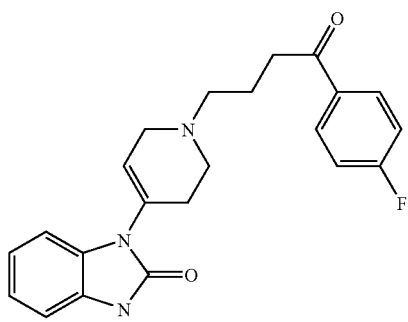

Compound 23

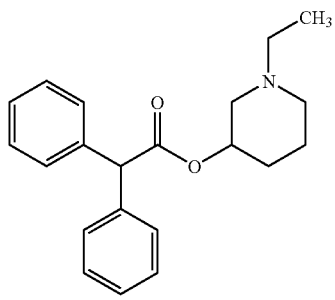

Compound 24

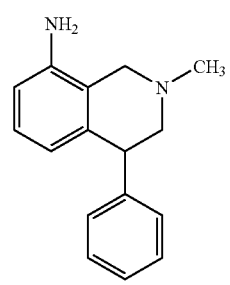

Compound 25

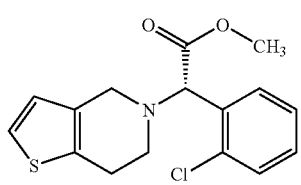

Compound 26

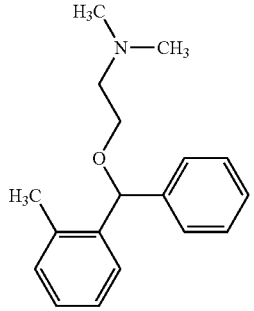

Compound 27

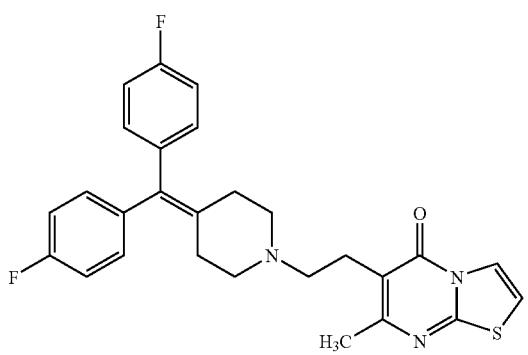

and pharmaceutically acceptable salts and complexes thereof.

Additional exemplary compounds that that may be used in accordance with the methods of the invention include, but are not limited to, the following:

Compound 28

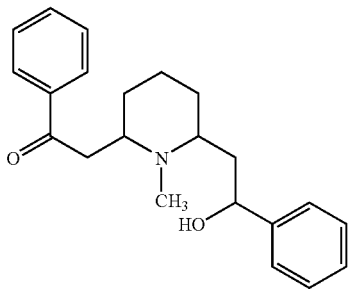

Compound 29

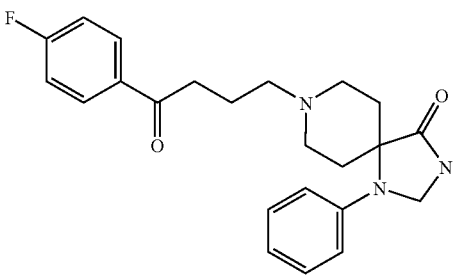

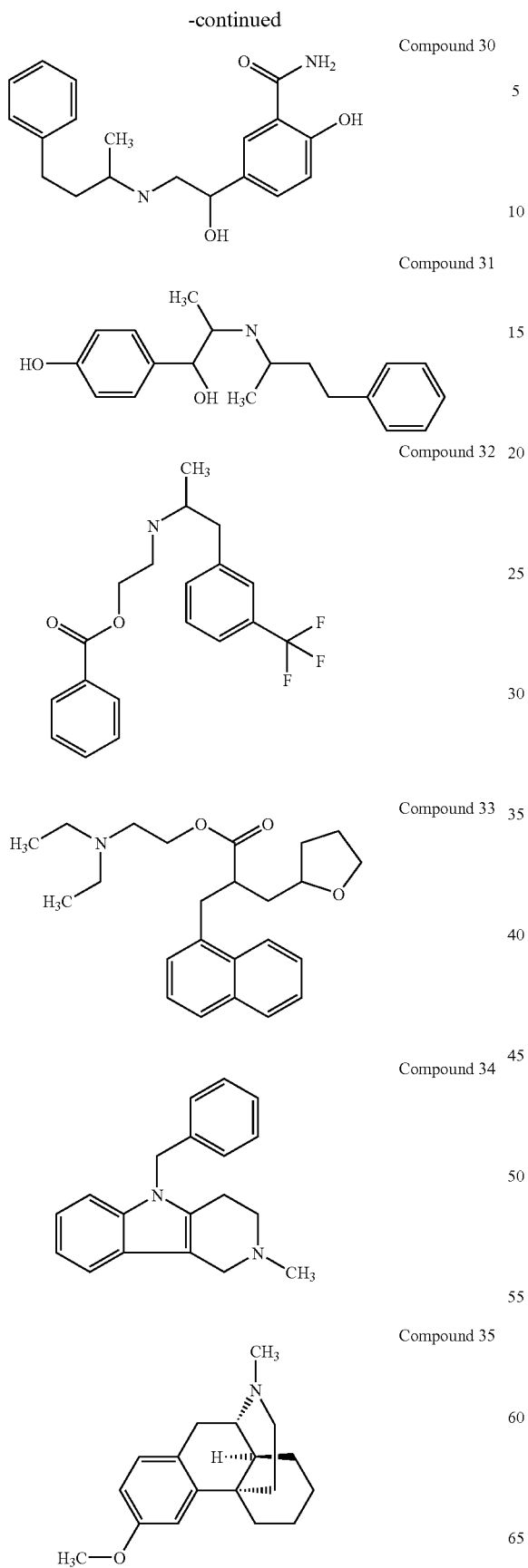

The exemplary compounds of the present invention were identified as being useful in the treatment of neurological diseases and disorders in a high throughput screening (HTS) system for compounds that improve the growth rate and/or prevent cell death in a cell line expressing low levels of SMN protein. In the SMN conditional knockout cell line, S5, the endogenous smn gene is disrupted by homologous recombination, and the SMN protein is stably expressed from an SMN cDNA under the control of a tetracycline (tet)-repressible promoter (Wang and Dreyfuss (2001) supra). Depletion of the SMN protein by addition of 1 μg/ml tet to the cell culture medium results in cell death within 72 to 96 hours. However, at lower concentrations of tetracycline, e.g., 18 ng/ml tet, cells contain significantly reduced, but not depleted, levels of SMN and exhibit a markedly reduced growth rate.

Libraries of compounds were screened against the S5 cell line. Typically, compounds were dissolved in DMSO and added to a final concentration of 10 μM to S5 cells that had been cultured with 18 ng/ml tet for 24 hours in 96-well plates. The cells were incubated for an additional 72 hours and the number of viable cells in each well was determined by measuring the ATP level in the cell lysate, a sensitive assay commonly used to assess cell viability in HTS (Crouch, et al. (1993) *J. Immunol. Methods* 160:81-88). The primary screen yielded over 100 active compounds. Activity of the compounds was measured as the difference between the sample and the average of the controls. Compounds with activities greater than two times the standard deviation of controls were further investigated.

To exclude false-positives, namely compounds that show increased cell growth because they antagonize the tet-induced repression, a parallel screen was carried out. This screen used DT40 cells which bear a conditional knockout of the asf/sf2 gene (ASF-DT40) engineered in the same manner as the S5 cell line (Wang, et al. (1996) *Genes Dev.* 10:2588-2599). Upon exposure to tetracycline, ASF/SF2 protein levels are reduced and ASF-DT40 cells exhibit a growth defect comparable to S5. An increase in cell number of both cell lines, S5 and ASF-DT40, upon exposure to a compound was indicative of an interference with the tet-repressor expression system. This parallel screen eliminated over 70% of the positive compounds identified in the primary screen. The remaining compounds were further examined.

Cell toxicity experiments revealed that eight of the compounds identified in the initial screen, Compounds 1-5 and 11-13, exhibited low cell toxicity at concentrations of 10 µM. The activities of all compounds were further examined at concentrations ranging from 0.5 to 20 µM. All compounds were found to be active and showed a dose-response profile. The activity of each compound was determined as a percentage increase of the ATP level, reflecting the number of viable cells, relative to cells treated with an equal volume of DMSO only. Table 1 provides the maximal activity and effective concentration for half maximum activity (EC50) of these compounds.

TABLE 1

| Compound Number | Maximum Activity (%) | EC50 (µM) |
|---|---|---|
| 1 | 30 | 3.0 |
| 2 | 30 | 3.0 |
| 3 | 60 | 5.0 |
| 4 | 35 | 4.0 |
| 5 | 75 | 5.0 |
| 6 | 50 | 2.5 |
| 7 | 45 | 3.0 |
| 8 | 25 | <1.0 |
| 9 | 50 | 1.5 |
| 10 | 30 | 3.0 |
| 11 | 60 | 2.5 |
| 12 | 75 | 2.5 |
| 13 | 70 | 3.0 |
| 14 | 40 | 2.5 |
| 15 | 70 | 2.0 |
| 16 | 60 | 1.0 |
| 17 | 80 | 1.5 |
| 18 | 25 | 1.5 |
| 19 | 30 | 2.0 |
| 20 | 35 | 1.0 |
| 21 | 55 | ND |
| 22 | 50 | ND |
| 23 | 50 | ND |
| 24 | 35 | ND |
| 25 | 100 | 7.0 |
| 26 | 45 | ND |
| 27 | 80 | ND |
| 28 | 30 | 3.0 |
| 29 | 140 | 4.0 |
| 30 | 60 | 5.0 |
| 31 | 60 | ND |
| 32 | 35 | ND |
| 33 | 90 | 3.0 |
| 34 | 70 | 3.5 |
| 35 | 60 | 6.5 |
| 36 | 70 | 3.5 |

To determine an accurate measure of the number of viable cells, cell numbers were also determined. In the presence of 10 ng/ml tet, S5 cells containing a comparable level of SMN to wild-type DT40 reached confluence in 72 hours. In contrast, S5 cells cultured with 18 ng/ml tet displayed a significant growth defect after 72 hours and cell death occurred between 72 and 96 hours. Overall, treatment with active compounds significantly increased the number of viable cells after 96 hours, the time course of the screen. Compounds 12 and 17 showed the highest activities; a three to four-fold increase in cell number over control cells treated with DMSO alone. Results from this assay were similar to those of the ATP assay.

SMN levels were also determined. Total cell lysates from treated cells were prepared and analyzed by immunoblotting with an anti-SMN antibody. S5 cells, cultured in the presence of 10-12 ng/ml tet, expressed comparable or slightly higher levels of SMN than the parental DT40 cells. However, in the presence of 18 ng/ml tet, a reduction in the amount of SMN was observed in S5 cells, which was approximately 15-20% of wild-type, a reduction comparable to that found in the cells of severely affected SMA patients. Cells treated with 4 µM of Compound 20, 16, or 17, the highest concentration at which there is no apparent cell toxicity, contain a similar level of SMN compared to control cells incubated with DMSO alone. The same blots were probed with antibodies against two other abundant proteins, Y14[30] and β-tubulin, to provide an internal control for the amount of cell lysate loaded on the gel. Protein loads were equal and the amount of SMN protein did not vary upon treatment with the compounds. Thus, these compounds do not interfere with the tet-repressor expression system. An alteration in SMN protein amounts in one particular sample, which had an equal protein load, would have indicated that the compound, for example, either had an effect on the tet-repressor system, as it directly regulates the expression of SMN protein, or had an effect on the accumulation of SMN protein by, for example significantly modifying the stability of SMN protein. The compounds disclosed herein increase cell growth and/or prevent cell death; further, these exemplary compounds alleviate or reduce this phenotype without modifying SMN protein levels. An advantage in using one of these exemplary compounds is their relatively favorable pharmacological profiles, their ability to cross the blood-brain barrier, and the wealth of clinical experience in their use.

As will be understood by those of skill in the art upon reading this disclosure, additional compounds to those exemplified herein may be identified routinely in accordance with the screening taught herein. Additional compounds for screening may be selected randomly by one skilled in the art and/or based upon their containing one of the three basic structures of Formula I through III or a structure similar to that of Compounds 28 through 40.

Though the teachings herein provide the S5 cell line for identifying useful agents, one of skill in the art can appreciate that any cell with low SMN protein levels may be used in the screens, assays, or kits provided herein. Moreover, any measurable molecular or cellular phenotype, in addition to those provided above, which is associated with low SMN proteins levels may be used in the screens, assays, or kits.

The HTS system provided herein can also be used to identify compounds for the treatment of psychiatric diseases and disorders including, for example, compounds exhibiting activity toward a component of a calmodulin (CaM) pathway.

Calmidazolium (CALBIOCHEM®, San Diego, Calif.), a calmodulin antagonist, improved the growth of S5 cells in the high-throughput screening system of the invention at concentrations as low as 215 nM. KN-93 (Compound 37; 2-[N-(2-hydroxyethyl)]-N-(4-methoxybenzenesulfonyl)]amino-N-(4-chlorocinnamyl)-N-methylbenzylamine, CALBIOCHEM®, San Diego, Calif.), an inhibitor of $Ca^{2+}$/CaM-dependent protein kinase II, also improved the growth of S5 cells. In contrast, KN-92 (2-[N-(4-Methoxybenzenesulfonyl)]amino-N-(4-chlorocinnamyl)-N-methylbenzylamine, CALBIOCHEM®, San Diego, Calif.), an inactive analog of KN-93, did not affect the growth of S5 cells. Other CaM antagonists such as W13 (Compound 38; N-(4-Aminobutyl)-5-chloro-1-naphthalenesulfonamide, CALBIOCHEM®, San Diego, Calif.), W5 (Compound 39; N-(6-Aminohexyl)-1-naphthalenesulfonamide, CALBIOCHEM®, San Diego, Calif.), and W7 (Compound 40; N-(4-Aminobutyl)-5-chloro-1-naphthalenesulfonamide, CALBIOCHEM®, San Diego, Calif.) also restored growth of S5 cells. Conversely, compounds active in improving growth of S5 cells did not increase the growth of cells expressing low levels of ASF/SF2 protein. Taken together, these results indicate that components of the CaM pathway modulate or interact with SMN.

Accordingly, another aspect of the invention provides a high-throughput screening kit and methods for using this kit to identify compounds or agents for the treatment of psychiatric diseases or disorders. The kit and method of the present invention are particularly useful in identifying psychopharmacological compounds that modulate a component of the CaM pathway.

In a preferred embodiment, kits of the present invention comprise, in separate containers, test cells, which have low SMN protein levels, and standard(s). Kits may also comprise buffers or growth media and an instructional brochure explaining how to use the kit. A preferred test cell for use in these kits comprises the S5 cell line provided above. As one of skill in the art will appreciate, a standard may comprise an agent which illustrates a positive outcome (i.e., positive standard) or a negative outcome (i.e., negative standard) to which an unknown test agent may be compared and indexed. As used herein, a positive standard is one which alleviates or reduces a phenotype of cells with low SMN protein levels (e.g., calmidazolium, KM-93, or W7) whereas a negative standard does not alter the phenotype of cells with low SMN protein levels (e.g., KN-92).

The invention also provides a method of identifying psychopharmacological compounds, also referred to herein as agents, by screening a library of agents with the high-throughput system of the invention. Such libraries may comprise either collections of pure agents or collections of agent mixtures. Examples of pure agents include, but are not limited to, proteins, polypeptides, peptides, nucleic acids, oligonucleotides, carbohydrates, lipids, synthetic or semi-synthetic chemicals, and purified natural products. Examples of agent mixtures include, but are not limited to, extracts of prokaryotic or eukaryotic cells and tissues, as well as fermentation broths and cell or tissue culture supernates. In the case of agent mixtures, the methods of this invention are not only used to identify those crude mixtures that possess the desired activity, but also provide the means to monitor purification of the active principle from the mixture for characterization and development as a therapeutic drug. In particular, the mixture so identified may be sequentially fractionated by methods commonly known to those skilled in the art which may include, but are not limited to, precipitation, centrifugation, filtration, ultrafiltration, selective digestion, extraction, chromatography, electrophoresis or complex formation. Each resulting subfraction may be assayed for the desired activity using the original assay until a pure, biologically active agent is obtained.

Library screening may be performed as exemplified herein or may be performed in any format that allows rapid preparation and processing of multiple reactions such as in, for example, multi-well plates of the 96-well variety. Stock solutions of the agents as well as cell lines and assay components are prepared manually and all subsequent pipetting, diluting, mixing, washing, incubating, sample readout and data collecting is done using commercially available robotic pipetting equipment, automated work stations, and analytical instruments for detecting the signal generated by the assay. Examples of such detectors include, but are not limited to, luminometers, spectrophotomers, calorimeters, and fluorimeters, and devices that measure the decay of radioisotopes.

The high-throughput screening system of the invention may be used to screen combinatorial libraries of random peptides, oligonucleotides or other chemical entities produced by any of the techniques already in the public domain or otherwise known to those skilled in the art. Because of their large size, these libraries are likely sources of lead agents since they can contain from 1 to $10^{10}$ chemical entities.

In a screen for a psychopharmacological agent one would measure changes in cellular phenotypes, associated with a dell having low levels of SMN protein, upon exposure to the agent being tested. Cellular phenotypes which may be measured typically include, but are not limited to, poor cell viability and/or proliferation and high cell death. Accordingly, agents which alleviate or reduce a cellular phenotype associated with low levels of SMN protein should increase viability and/or proliferation and decrease cell death. Once an agent has been identified that alleviates or reduces a phenotype of a cell expressing low levels of SMN protein, the agent may be tested in a cell expressing low levels of ASF/SF2 protein. Furthermore, the agent may be tested for its ability to alter or modulate the levels of SMN protein or alter or modulate protein levels or activities of components of the calmodulin pathway, e.g., calmodulin (CaM) or $Ca^{2+}$/CaM-dependent protein kinase II (CaMKII). Protein levels may be assessed using standard techniques such as immunoassays and antibodies specific to the protein being analyzed. Protein activities also may be monitored using well-known methodologies such as the SIGNATECT® CAMKII Assay System (PROMEGA®, Madison, Wis.).

Psychopharmacological agents and neurodegenerative agents identified in accordance with the present invention may be tested for utility in treating neurological disorders. Such testing is performed initially in model systems of the disorder of interest, and subsequently in human subjects. The adsorption, distribution, metabolism and excretion of the agent are characterized, and its potential toxicity is assessed in acute, sub-chronic and chronic studies.

Compounds of the present invention including those identified using the screening method and kit of the invention may be incorporated into pharmaceutical compositions and used in the treatment of neurological diseases and disorders. Treatment involves the steps of first identifying a patient that suffers from a neurological disease or disorder by standard clinical methodologies and then administering to the patient a pharmaceutical composition comprising a compound of the present invention. Pharmaceutical compositions may be in the form of pharmaceutically acceptable salts and complexes and may be provided in a pharmaceutically acceptable carrier and at an appropriate dose.

Examples of pharmaceutically acceptable salts include, but are not limited to, salts prepared from pharmaceutically acceptable acids or bases, including organic and inorganic acids and bases. When the preferred compound of use is basic, salts may be prepared from pharmaceutically acceptable acids. Suitable pharmaceutically acceptable acids include acetic, benzenesulfonic (besylate), benzoic, p-bromophenylsulfonic, camphorsulfonic, carbonic, citric, ethanesulfonic, fumaric, gluconic, glutamic, hydrobromic, hydrochloric, hydroiodic, isethionic, lactic, maleic, malic, mandelic, methanesulfonic (mesylate), mucic, nitric, oxalic, pamoic, pantothenic, phosphoric, succinic, sulfuric, tartaric, p-toluenesulfonic, and the like. Examples of such pharmaceutically acceptable salts include, but are not limited to, acetate, benzoate, hydroxybutyrate, bisulfate, bisulfite, bromide, butyne-1,4-dioate, carpoate, chloride, chlorobenzoate, citrate, dihydrogenphosphate, dinitrobenzoate, fumarate, glycollate, heptanoate, hexyne-1,6-dioate, hydroxybenzoate, iodide, lactate, maleate, malonate, mandelate, metaphosphate, methanesulfonate, methoxybenzoate, methylbenzoate, monohydrogenphosphate, naphthalene-1-sulfonate, naphthalene-2-sulfonate, oxalate, phenylbutyrate, phenylproionate, phosphate, phthalate, phylacetate, propanesulfonate, propiolate, propionate, pyrophosphate, pyrosulfate, sebacate, suberate, succinate, sulfate, sulfite, sulfonate, tartrate, xylenesulfonate, and the like.

Compounds of the present invention may be conveniently administered in a pharmaceutical composition containing the active compounds in combination with a suitable carrier. Such pharmaceutical compositions may be prepared by methods and contain carriers which are well known in the art. A generally recognized compendium of such methods and ingredients is Remington's Pharmaceutical Sciences (A. R. Gennaro ed. 1985. Mack Publishing Co.). A pharmaceutically-acceptable carrier, composition or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the patient.

Examples of materials which can serve as pharmaceutically-acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The compositions of the present invention may be administered parenterally (for example, by intravenous, intraperitoneal, subcutaneous or intramuscular injection), topically (including buccal and sublingual), orally, intranasally, intravaginally, or rectally, with oral administration being particularly preferred.

For oral therapeutic administration, the composition may be combined with one or more carriers and used in the form of ingestible tablets, buccal tablets, troches, capsules, elixirs, suspensions, syrups, wafers, chewing gums, foods and the like. Such compositions and preparations should contain at least 0.1% of active compound. The percentage of the compositions and preparations may, of course, be varied and may conveniently be between about 0.1 to about 100% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. The above listing is merely representative and one skilled in the art could envision other binders, excipients, sweetening agents and the like. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like.

A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active components may be incorporated into sustained-release preparations and devices including, but not limited to, those relying on osmotic pressures to obtain a desired release profile. Once daily formulations for each of the active components are specifically included.

The selection of the dosage or effective amount of a compound of the invention is that which has the desired outcome of reducing the signs or symptoms of a neurological disease or disorder in a patient. For example, a compound of the invention may reduce the signs or symptoms of neurodegeneration by replacing or enhancing the function or SMN or by alleviating or reducing a cellular phenotype associated with low levels of SMN protein. Signs or symptoms of neurodegeneration which may be reduced include, but are not limited to, tremor, muscular rigidity, difficulty in initiating motor activity, loss of postural reflexes, involuntary movements, gait disturbance, personality changes, memory loss, relentless muscle wasting, and weakness involving limb and bulbar musculature.

Compounds identified by the high-throughput screening system of the present invention may be used to reduce the signs or symptoms of a psychiatric disease or disorder. General signs and symptoms associated with such neurological disorders include, but are not limited to, depression, hyperactivity, inattention, impulsivity, distractibility, phobias, panic attacks, anxiety, compulsive behaviors, addictions and substance, abuse and overeating.

The selected dosage level will depend upon a variety of factors including the activity of the particular compound of the present invention employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. This is considered to be within the skill of the artisan and one can review the existing literature on a specific compound to determine optimal dosing.

In general, the daily dose contains from about 0.1 mg to about 2000 mg. More preferably, each dose of a compound contains about 0.5 to about 60 mg of the active ingredient. This dosage form permits the full daily dosage to be administered in one or two oral doses. More than once daily or twice daily administrations, e.g., 3, 4, 5 or 6 administrations per day, are also contemplated herein.

In general, the average daily adult dosage of compounds disclosed herein is as follows. The dosages expressly include all numerical values, whole or fractional, within the stated range. Pediatric and doses for elderly patients may be more or less than the daily dosages provided herein. Compound Average Daily Dosage (mg/day/patient): Compound 1, 75 to 300; Compound 2, 24 to 300; Compound 3, 75 to 300; Compound 4, 75 to 300; Compound 5, 30 to 120; Compound 6, 60 to 300; Compound 7, 30 to 60; Compound 8, 50 to 300; and Compound 9, 25 to 250; Compound 10, 25 to 900; Compound 11, 60 to 1000; Compound 12, 10 to 100; Compound 13, 15 to 150; Compound 14, 30 to 100; Compound 15, 50 to 600; Compound 16, 10 to 40; Compound 17, 30 to 800; Compound 18, 1 to 150; Compound 19, 6 to 60; Compound 20, 25 to 900; Compound 21, 100 to 200; Compound 22, 1 to 125; Compound 23, 20 to 200; Compound 24, 1 to 80; Compound 25, 75 to 600; Compound 26, 200 to 300; Compound 27, 10 to 50; Compound 29, 1 to 600; Compound 30, 0.5 to 10; Compound 31, 200 to 2400; Compound 32, 5 to 50; Compound 33, 10 to 100; Compound 34, 300 to 600; Compound 35, 100 to 300; Compound 36, 40 to 120; and Compound 37, 40 to 200.

The compounds disclosed herein are used to treat neurodegenerative diseases or disorders, Treatment of the such diseases or disorders is accomplished by delivering an effective amount of a composition disclosed herein to a mammal. In most cases this will be a human being, but treatment of food animals, e.g., livestock and poultry, and companion animals, e.g., dogs, cats and horses, is expressly covered herein.

The invention is described in greater detail by the following non-limiting examples.

Example 1

S5 Cell Line

As SMN may be required for cell viability, a DT40 cell line (ATCC# CRL-2111), termed C2, which expresses cSMN protein from a cDNA under the control of a tet-repressible promoter (Gossen and Bujard (1992) Proc. Natl. Acad. Sci. U.S.A. 89:5547-5551) was generated. To express cSMN cDNA from a tetracycline-repressible promoter, two plasmid constructs were used, Puro-tTA and 108-cSMN. Puro-tTA containing a cDNA encoding VP16-tetR chimeric protein (Gossen and Bujard (1992) ibid.) under the control of the chicken-actin promoter, as well as a puromycin resistance gene, are known in the art (Wang, et al. (1996) supra). 108-cSMN contains a full-length cSMN cDNA (Accession no. AF322650) digested with NcoI/XhoI and inserted into the SalI site of p108-His (Gossen and Bujard (1992) id.) just downstream of tetO-CMV minimal promoter and a histidinol resistance gene.

DT40 were maintained in RPMI 1640 medium (Life Technologies, Inc., Carlsbad, Calif.) containing 10% fetal bovine serum (Hyclone, Logan, Utah), 1% chicken serum (SIGMA®, St. Louis, Mo.), 2 mM L-glutamine, and 50 μM 2-mercaptoethanol. DT40 cells were transfected by electroporation using standard methods (Buerstedde and Takeda (1991) Cell 67:179-188). To express cSMN cDNA from a tetracycline-repressible promoter, DT40 cells were cotransfected with Puro-tTA and 108-cSMN and selected in medium containing puromycin and histidinol. Concentrations of antibiotics or drugs used were: 1.5 mg/ml hygromycin B (CALBIOCHEM®, San Diego, Calif.), 1 mg/ml histidinol (SIGMA®, St. Louis, Mo.), 0.5 μg/ml puromycin (SIGMA®, St. Louis, Mo.). Tetracycline hydrochloride was used as indicated by the manufacturer (SIGMA®, St. Louis, Mo.). The resulting C2 cells, maintained in a medium containing 10 ng/ml tet, showed normal growth and expressed high levels of exogenous cSMN protein. Thus, knockout of the cSMN gene was carried out in C2 cells cultured in the presence of 10 ng/ml tet.

To generate the S5 cell line from C2, the hygromycin resistance gene, under the control of the chicken-actin promoter, was digested with XhoI/HindIII and inserted into the BsmI/PvuII sites of the chicken SMN (cSMN) genomic DNA (GENBANK™ accession number AF322650), replacing the entire exon 3 and part of exon 4 of the cSMN gene. C2 cells were transfected with linearized Hyg-SMN plasmid DNA by electroporation and selected in hygromycin-containing medium. Genomic DNA was extracted from hygromycin-resistant clones, digested with XbaI, and subjected to Southern blot analysis to identify a strain that had a homologous recombination event at the SMN locus.

Example 2

Tissue Culture

The chicken pre-B cell line DT40, the smn conditional knockout cell line S5 and the asf/sf2 conditional knockout cell line ASF-DT40 (Wang, et al. (1996) supra) were maintained using known methods (Wang and Dreyfuss (2001) supra). To reduce the SMN level, S5 cells were incubated with 18 ng/ml tetracycline hydrochloride (tet). Similarly, ASF-DT40 cells were treated with 14 ng/ml tet to partially deplete the ASF/SF2 protein.

Example 3

High Throughput Screen (HTS)

Automated liquid handling was performed on a BIOMEK® 2000 workstation (Beckman-Coulter, Inc., Fullerton, Calif.). Chemical compound libraries were purchased from MicroSource Discovery Systems, Inc. (Gaylordsville, Conn.). The original libraries were supplied as 10 mM solution in dimethyl sulphoxide (DMSO) formatted in 96-well master plates. The libraries were diluted in DMSO to achieve the final concentration of 3 mM.

After being incubated in medium containing 18 ng/ml tet for 24 hours, S5 cells were dispensed into 96-well plates at 120 µl per well. Compounds were added to these cells by pipetting 0.4 µl of the 3 mM libraries into each well to reach a final concentration of 10 µM. The 96-well plates were further incubated for 72 hours at 37° C. with 5% $CO_2$. Subsequently, the level of cellular ATP in each well was measured using the CELLTITER-GLO™ Luminescent Cell Viability Assay kit (PROMEGA®, Madison, Wis.) according to the manufacturer's instructions. Luminescence was read on a Wallac Victor2 multi-channel plate reader (Perkin-Elmer, Boston, Mass.). The cellular ATP level is a direct measure of the number of viable cells in each well (Crouch, et al. (1993) supra). Data from luminescence readings were analyzed with MICROSOFT® Excel.

Example 4

Western Blot Analysis

Western blots were performed to determine if the expression of SMN protein was being altered by exposure to the compounds disclosed herein. Western blot analysis of SMN protein was performed using standard methods (Charroux, et al. (1999) supra).

What is claimed is:

1. A method of treating a neurodegenerative disease or disorder with low SMN protein levels comprising administering an effective amount of a compound that replaces or enhances the function of SMN to alleviate or reduce a phenotype of cells with low SMN protein levels, wherein said neurodegenerative disease or disorder is spinal muscular atrophy and further wherein said compound is selected from the group consisting of:

Compound 11

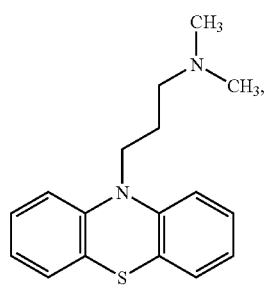

Compound 12

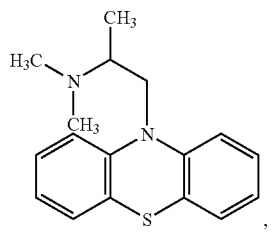

Compound 13

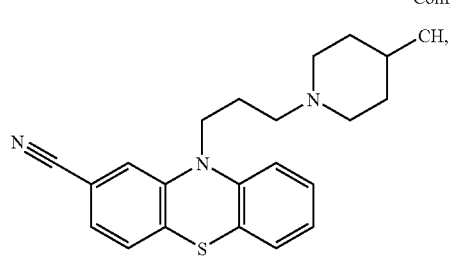

Compound 14

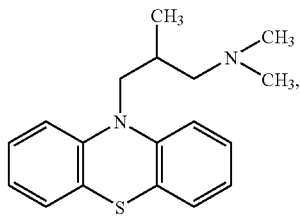

Compound 15

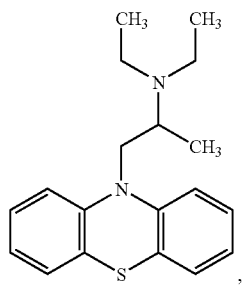

Compound 16

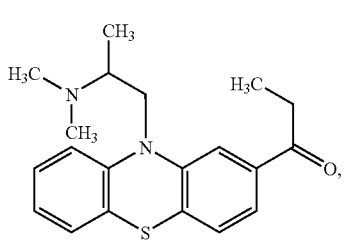

-continued
Compound 17
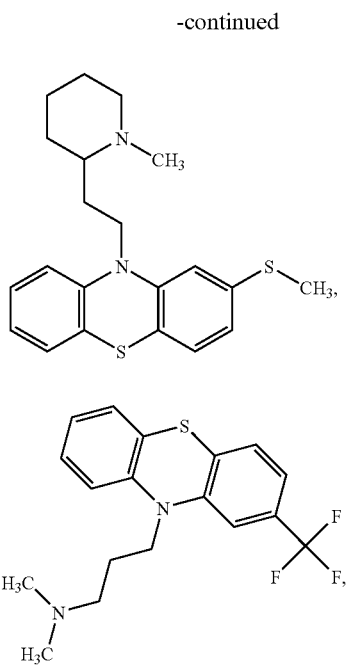
Compound 18
Compound 19
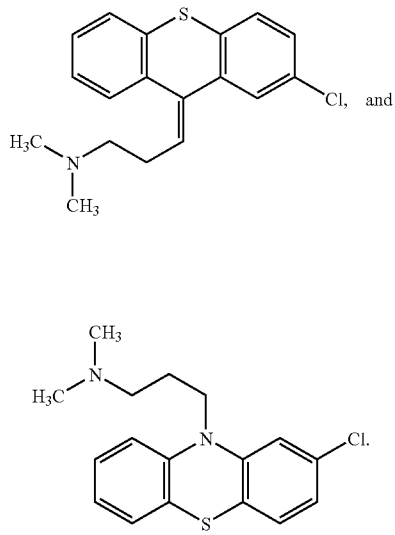
Compound 20
* * * * *